US007919283B2

(12) United States Patent
Filippov et al.

(10) Patent No.: US 7,919,283 B2
(45) Date of Patent: Apr. 5, 2011

(54) METHOD FOR PRODUCING AN L-AMINO ACID USING A BACTERIUM OF THE ENTEROBACTERIACEAE FAMILY WITH ATTENUATED EXPRESSION OF ANY OF THE CYNT, CYNS, CYNX OR CYNR GENE OR COMBINATION THEREOF

(75) Inventors: Dmitriy Vladimirovich Filippov, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/469,334

(22) Filed: May 20, 2009

(65) Prior Publication Data
US 2009/0269819 A1 Oct. 29, 2009

Related U.S. Application Data

(63) Continuation of application No. PCT/JP2007/073887, filed on Dec. 3, 2007.

(30) Foreign Application Priority Data

Dec. 12, 2006 (RU) .............................. 2006143864

(51) Int. Cl.
C12P 13/04 (2006.01)
C12N 9/00 (2006.01)
C12N 1/20 (2006.01)
C12N 15/00 (2006.01)
C07H 21/02 (2006.01)

(52) U.S. Cl. .................... 435/106; 435/183; 435/252.3; 435/320.1; 536/23.1

(58) Field of Classification Search .......................... None
See application file for complete search history.

(56) References Cited

U.S. PATENT DOCUMENTS

| | | | |
|---|---|---|---|
| 5,175,107 A | 12/1992 | Debabov et al. | |
| 5,688,671 A | 11/1997 | Sugimoto et al. | |
| 5,830,716 A | 11/1998 | Kojima et al. | |
| 5,932,453 A | 8/1999 | Kikuchi et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 7,138,266 B2 | 11/2006 | Debabov et al. | |
| 7,186,531 B2 | 3/2007 | Akhverdian et al. | |
| 7,259,003 B2 | 8/2007 | Livshits et al. | |
| 7,312,058 B2 | 12/2007 | Kashiwagi et al. | |
| 7,381,548 B2 | 6/2008 | Sheremet'eva et al. | |
| 7,422,880 B2 | 9/2008 | Rybak et al. | |
| 7,476,531 B2 | 1/2009 | Tabolina et al. | |
| 7,531,332 B2 | 5/2009 | Livshits et al. | |
| 2002/0110876 A1 | 8/2002 | Miyata et al. | |
| 2004/0132165 A1 | 7/2004 | Akhverdian et al. | |
| 2005/0214911 A1 | 9/2005 | Marchenko et al. | |
| 2005/0239177 A1 | 10/2005 | Livshits et al. | |
| 2006/0088919 A1 | 4/2006 | Rybak et al. | |
| 2006/0216796 A1 | 9/2006 | Hashiguchi et al. | |
| 2007/0004014 A1 | 1/2007 | Tsuji et al. | |
| 2008/0113416 A1 | 5/2008 | Filippov et al. | |
| 2008/0261278 A1 | 10/2008 | Tabolina et al. | |
| 2008/0261279 A1 | 10/2008 | Tabolina et al. | |
| 2009/0081738 A1 | 3/2009 | Filippov et al. | |
| 2009/0087886 A1 | 4/2009 | Filippov et al. | |
| 2009/0098621 A1 | 4/2009 | Rybak et al. | |
| 2009/0117623 A1 | 5/2009 | Marchenko et al. | |

FOREIGN PATENT DOCUMENTS

| WO | WO2006/123763 | 11/2006 |
|---|---|---|
| WO | WO2008/072640 | 6/2008 |

OTHER PUBLICATIONS

Anderson, P. M., et al., "The cyanase operon and cyanate metabolism," FEMS Microbiol. Rev. 1990;87:247-252.
Debabov, V. G., et al.: Advances in Biochemical Engineering, Biotechnology 2003;79:113-136.
Guilloton, M. B., et al., "A Physiological Role for Cyanate-Induced Carbonic Anhydrase in *Escherichia coli*," J. Bacteriol. 1993;175(5):1443-1451.
Hashimoto, M., et al., "Indispensibility of the *Escherichia coli* Carbonic Anhydrases YadF and CynT in Cell Proliferation at a Low $CO_2$ Partial Pressure," Biosci. Biotechnol. Biochem. 2003;67(4):919-922.
Kozliak, E. I., et al., "Role of Bicarbonate/$CO_2$ in the Inhibition of *Escherichia coli* Growth by Cyanate," J. Bacteriol. 1995 ; 177(11):3213-3219.
Kozliak, E. I., et al., "Expression of Proteins Encoded by the *Escherichia coli* cyn Operon: Carbon Dioxide-Enhanced Degradation of Carbonic Anhydrase," J. Bacteriol. 1994;176(18):5711-5717.
Merlin, C., et al., "Why Is Carbonic Anhydrase Essential to *Escherichia coli*?" J. Bacteriol. 2003;185(21):6415-6424.
Mitsuhashi, S., et al., "A gene homologous to β-type carbonic anhydrase is essential for the growth of Corynebacterium glutamicum under atmospheric conditions," Appl. Microbiol. Biotechnol. 2004;63:592-601.
International Search Report and Written Opinion of the International Searching Authority for PCT Patent App. No. PCT/JP2007/073887 (Mar. 5, 2008).
Guilloton, M. B., et al., "Carbonic Anhydrase in *Escherichia coli*" J. Biol. Chem. 1992;267(6):3731-3734.
Lamblin, A. J., et al., "Expression and Purification of the cynR-Regulatory Gene Product: CynR Is a DNA-Binding Protein" J. Bacteriol. 1993;175(24):7990-7999.
Lamblin, A. J., et al., "Functional Analysis of the *Escherichia coli* K-12 cyn Operon Transcriptional Regulation" J. Bacteriol. 1994;176(21):6613-6622.

(Continued)

Primary Examiner — Christian L Fronda
(74) Attorney, Agent, or Firm — Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of one or more of the cynT, cynS, cynX and/or cynR genes.

3 Claims, 2 Drawing Sheets

OTHER PUBLICATIONS

Little, R. M., et al, "Structual Properties of Cyanase Denaturation, Renaturation, and Role of Sulfhydryls and Oligomeric Structure in Catalytic Activity" J. Biol. Chem. 1987;262(21):10120-10126.

Pao, S. S., et al., "Major Facilitator Superfamily" Microbiol. Molecul. Biol. Rev. 1998;62(1):1-34.

Sung, Y., et al., "Characterization of the *cyn* Operon in *Escherichia coli* K-12" J. Biol. Chem 1988;263(29):14769-14775.

Sung, Y-C, et al., "The *Escherichia coli* K-12 *cyn* Operon Is Positively Regulated by a Member of the *lysR* Family," J. Bacteriol. 1992;174(11):3645-3650.

International Preliminary Report on Patentability for PCT Patent App. No. PCT/JP20071073887 (Jun. 25, 2009).

US 7,919,283 B2

METHOD FOR PRODUCING AN L-AMINO ACID USING A BACTERIUM OF THE ENTEROBACTERIACEAE FAMILY WITH ATTENUATED EXPRESSION OF ANY OF THE CYNT, CYNS, CYNX OR CYNR GENE OR COMBINATION THEREOF

This application is a continuation under 35 U.S.C. §120 to PCT Patent Application No. PCT/JP2007/073887, filed on Dec. 3, 2007, which claims priority under 35 U.S.C. §119 to Russian Patent Application No. 2006143864, filed Dec. 12, 2006, both of which are incorporated by reference. The Sequence Listing filed electronically herewith is also hereby incorporated by reference in its entirety (File Name: US-303_Seq_List; File Size: 26 KB; Date Created: May 19, 2009).

BACKGROUND OF THE INVENTION

1. Technical Field

The present invention relates to the microbiological industry, and specifically to a method for producing an L-amino acid using a bacterium of the Enterobacteriaceae family which has been modified to attenuate expression of the cynTSX operon and the cynR gene.

2. Background Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042, or U.S. Pat. Nos. 4,346,170; 5,661,012 and 6,040,160).

Another way to enhance L-amino acid production yields is to attenuate expression of a gene, or several genes, involved in the degradation of the target L-amino acid, genes diverting the precursors of the target L-amino acid from the L-amino acid biosynthetic pathway, genes involved in the redistribution of carbon, nitrogen, and phosphate fluxes, and genes coding for toxins etc.

It is known that cyanate, a toxic compound, is the product of the spontaneous dissociation of urea in solution as well as of the decomposition of carbamoyl phosphate, an intermediate in the pyrimidine and arginine biosynthetic pathways. In *Escherichia coli*, the process of cyanate detoxication is mediated throught the cynTSX operon that enables *E. coli* to degrade and use cyanate as the sole nitrogen source. (Sung Y.-C. et. al., J. Biol. Chem.; 263(29):14769-14775 (1988)). The cynTSX operon which contains three genes: cynT, cynS, and cynX is transcribed as a polycistronic message. The cynTSX operon is inducible by cyanate and is under the control of the inducer gene cynR. This operon is also subject to catabolite repression by bicarbonate.

The product of the cynT gene of the cyn operon in *Escherichia coli* has been identified as a carbonic anhydrase. The cyn operon also includes the gene cynS, encoding the enzyme cyanase. Cyanase catalyzes the reaction of cyanate with bicarbonate to give ammonia and carbon dioxide. The carbonic anhydrase was isolated from an *Escherichia coli* strain overexpressing the cynT gene and characterized. The purified enzyme was shown to contain 1 $Zn^{2+}$/subunit (24 kDa) and was found to behave as an oligomer in solution; the presence of bicarbonate resulted in partial dissociation of the oligomeric enzyme. The kinetic properties of the enzyme are similar to those of carbonic anhydrases from other species, including inhibition by sulfonamides and cyanate. The amino acid sequence shows a high degree of identity with the sequences of two plant carbonic anhydrases but not with animal and algal carbonic anhydrases. Since carbon dioxide formed in the bicarbonate-dependent decomposition of cyanate diffuses out of the cell faster than it would be hydrated to bicarbonate, the apparent function of the induced carbonic anhydrase is to catalyze hydration of carbon dioxide and thus prevent depletion of cellular bicarbonate (Guilloton M. B. et. al., J. Biol. Chem.; 267(6):3731-4 (1992)).

Cyanase CynS is composed of 8-10 identical subunits (Mr=17,008) with significant amounts of α-helix and β-sheet structures, which catalytic activity links to the structural integrity of the oligomer (Little R. M. et a., J. Biol. Chem.; 262(21):10120-10126 (1987)).

The cynX gene encodes hydrophobic protein CynX with undetermined function. Based exclusively on degrees of sequence similarity, CynX has been determined to be a member of the major facilitator superfamily (MFS), which is one of the two largest families of membrane transporters and is present ubiquitously in bacteria, archaea, and eukarya, as a putative cyanate transporter (Pao S. S., Microbiol. And Mol. Biol. Rev.; 62(1):1-34 (1998)).

The physiological role of cynT, cynS and cynX was investigated by construction of chromosomal mutants in which these genes were rendered inactive. The delta cynT chromosomal mutant expressed an active cyanase but no active carbonic anhydrase. In contrast to the wild-type strain, the growth of the delta cynT strain was inhibited by cyanate, and the mutant strain was unable to degrade cyanate and therefore could not use cyanate as the sole nitrogen source when grown at a partial $CO_2$ pressures ($pCO_2$) of 0.03% (air). At a high $pCO_2$ (3%), however, the delta cynT strain behaved like the wild-type strain; it was significantly less sensitive to the toxic effects of cyanate and could degrade cyanate and use cyanate as the sole nitrogen source for growth. These results are consistent with the proposed function for carbonic anhydrase (Guilloton M. B. et. al., J. Bacteriol.; 175(5):1443-51 (1993)).

It was found that the carbonic anhydrase YadF is essential for cell growth in the absence of another carbonic anhydrase, CynT, in *Escherichia coli*. However, mutant strains lacking both of them grew at high $CO_2$ concentrations (5%), where non-enzymatic mechanisms generate $HCO_3^-$. This suggests that these carbonic anhydrases are essential because they maintain $HCO_3^-$ levels at ambient $CO_2$ concentrations (Hashimoto M., and Kato J., Biosci. Biotechnol. Biochem.; 67(4):919-22 (2003)).

CynT is the single *E. coli* Can (previously YadF) paralog. It can, when induced with azide, replace Can (Merlin C., et. al., J. Bacteriol.; 185(21):6415-24 (2003)).

Expression of the cynTSX operon is controlled by the CynR protein encoded by the cynR gene and transcribed in the direction opposite to that of the cyn operon (Lamblin A.-F. J., et. al., J. Bacteriol.; 175(21):7990-7999 (1993)). Analysis of the β-galactosidase transcriptional fusion suggest that CynR is a dual transcriptional regulator that belongs to the LysR family and is negatively autoregulated independently of cyanate (Sung Y.-C., et al., J. Bacteriol.; 174(11):3645-3650 (1992)). CynR is 32,000 Mr protein that recognizes a 136-bp DNA fragment encompassing the cynR-cynTSX intergenic region. Circular permutation assays indicated that CynR induces bending of the DNA upon binding and that this bending decreases in the presence of cyanate (Lamblin A.-F. J., et. al., J. Bacteriol.; 176(21):6613-6622 (1994)).

But currently, there have been no reports of attenuating expression of the cynTSX operon and the cynR gene for the purpose of producing L-amino acids.

SUMMARY OF THE INVENTION

Aspects of the present invention include enhancing the productivity of L-amino acid-producing strains and providing a method for producing an L-amino acid using these strains.

The above aspects were achieved by finding that attenuating expression of the cynTSX operon and the cynR gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family which has an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of a gene selected from the group consisting of cynT, cynS, cynX, cynR, and combinations thereof.

It is a further aspect of the present invention to provide the bacterium as described above, wherein the expression is attenuated by inactivation of the gene(s).

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide a method for producing an L-amino acid comprising:
cultivating the bacterium as described above in a medium, and
collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DETAILED DESCRIPTION OF THE PREFERRED EMBODIMENTS

1. Bacterium

Figure 1:
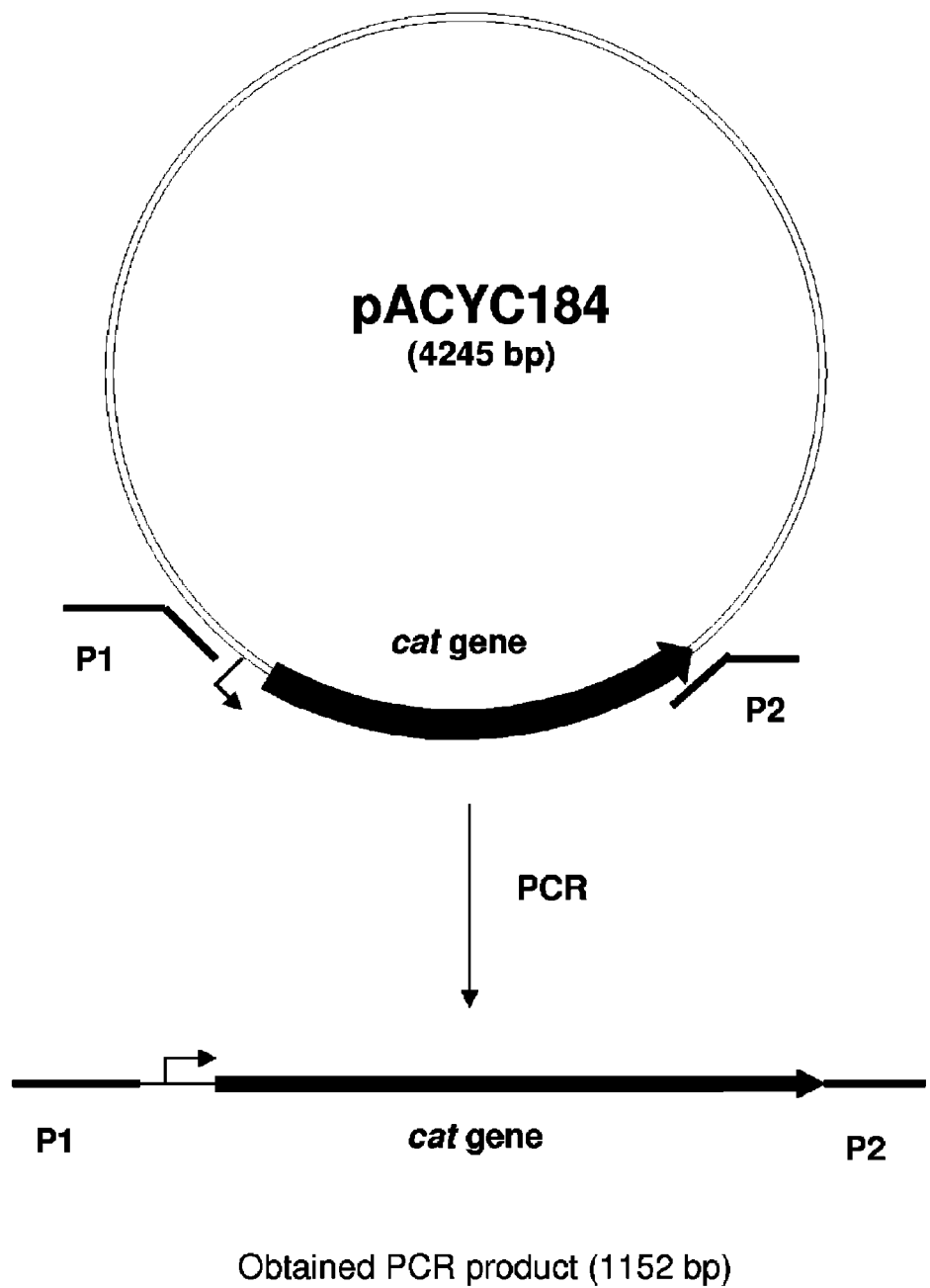
FIG. 1 shows the relative positions of primers P1 and P2 on plasmid pACYC184, which is used for amplification of the cat gene.

Exemplary embodiments of the bacterium of the present invention include L-amino acid-producing bacteria of the Enterobacteriaceae family, wherein the bacterium has been modified to attenuate expression of one or more of the cynT, cynS, cynX and cynR genes.

"L-amino acid-producing bacterium" means a bacterium which has an ability to produce and secrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of the bacterium, for example, *E. coli*, such as *E. coli* K-12, and preferably means that the bacterium is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are exemplary embodiments.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae family according to the taxonomy used by the NCBI (National Center for Biotechnology Information) database (http://www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus

*Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of a gene(s)" means that the bacterium has been modified in such a way that the modified bacterium contains a reduced amount of protein(s) encoded by the gene(s) as compared with an unmodified bacterium, or the modified bacterium is unable to synthesize protein(s) encoded by the gene(s). The phrase "bacterium has been modified to attenuate expression of a gene(s)" also include that the bacterium has been modified in such a way that the modified gene encodes a mutant protein(s) which has/have a decreased activity.

The phrase "inactivation of gene(s)" means that the modified gene(s) encode(s) a completely inactive protein(s). It is also possible that the modified DNA region is unable to naturally express the gene due to a deletion of a part of the gene or the gene entirely, a shifting of the reading frame of the gene, the introduction of missense/nonsense mutation(s), or the modification of an adjacent region of the gene, including the sequences controlling gene expression, such as the promoter(s), enhancer(s), attenuator(s), ribosome-binding site(s), etc.

The cynTSX operon is transcribed as a polycistronic mRNA including messages from all three genes. So modification of the first cynT gene, such as deletion of the whole or a part of the cynT gene, or introducing a stop codon or frame shift, could also lead to inactivation of the downstream genes.

The level of gene expression can be determined by measuring the amount of mRNA transcribed from the gene using various known methods including Northern blotting, quantitative RT-PCR, and the like.

The cynTSX operon includes three genes in the following order. The cynT gene (synonyms—ECK0336, b0339) encodes the CynT protein, a carbonic anhydrase monomer (synonym—B0339). The cynT gene (nucleotide positions: 358,023 to 358,682; GenBank accession no. NC_000913.2; gi: 49175990) is located between the cynR gene and the cynS gene on the *E. coli* K-12 chromosome. The cynS gene (synonyms—ECK0337, b0340, cnt, cyaN) encodes the CynS protein, a cyanase monomer (synonyms—B0340, Cnt, CyaN, CynS, cyanate hydrolase, cyanase, cyanate C—N-lyase). The cynS gene (nucleotide positions: 358,713 to 359,183; GenBank accession no. NC_000913.2; gi: 49175990) is located between the cynT gene and the cynX gene on the *E. coli* K-12 chromosome. The cynX gene (synonyms—ECK0338, b0341) encodes the CynX protein, a putative cyanate MFS transporter (synonym—B0341). The cynX gene (nucleotide positions: 359,216 to 360,370; GenBank accession no. NC_000913.2; gi: 49175990) is located between the cynS gene and the lacA gene on the *E. coli* K-12 chromosome. Examples of the cynT, cynS, and cynX genes from *Escherichia coli* are represented by SEQ ID NO: 1, SEQ ID NO: 3, and SEQ ID NO: 5, respectively. The amino acid sequences encoded by the genes of cynT, cynS, and cynX are represented by SEQ ID NO: 2, SEQ ID NO: 4, and SEQ ID NO: 6, respectively.

The cynR gene (synonyms—ECK0335, b0338) encodes the CynR protein, a dual transcriptional regulator that belongs to the LysR family (synonyms—B0338, CynR, cyn operon positive regulator). The cynR gene (nucleotides complementary to nucleotides 357015 to 357914 in the sequence of GenBank accession no. NC_000913.2; gi: 49175990) is located between the codA gene and the cynT gene on the *E. coli* K-12 chromosome. The nucleotide sequence of the cynR gene and the encoded CynR amino acid sequence are shown in SEQ ID NO: 7 and SEQ ID NO: 8, respectively.

Since there may be some differences in DNA sequences between the genera or strains of the Enterobacteriaceae family, the gene to be inactivated on the chromosome is not limited to the genes shown in SEQ ID Nos: 1, 3, 5 and 7 but may include genes homologous to SEQ ID Nos: 1, 3, 5 and 7 which encode variant proteins of the CynT, CynS, CynX and CynR proteins. The phrase "variant proteins" means proteins which have changes in the sequences, whether they are deletions, insertions, additions, or substitutions of amino acids.

The number of changes in the variant proteins depends on the position in the three dimensional structure of the protein or the type of amino acid residues. It may be 1 to 30, another example is 1 to 15, and another example is 1 to 5 in SEQ ID NOs: 2, 4, 6 and 8. These changes in the variants are conservative mutations that preserve the function of the protein. In other words, these changes in the variants can occur in regions of the protein which are not critical for the three dimensional structure of the protein. This is because some amino acids have high homology to one another so the three dimensional structure is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Substitutions, deletions, insertions, additions, or inversions and the like of the amino acids described above include naturally occurred mutations (mutant or variant) depending on differences in species, or individual differences of microorganisms that retain the cynT, cynS, cynX, or cynR gene. Such a gene can be obtained by modifying the nucleotide sequence shown in SEQ ID NO: 1, 3, 5, or 7 using, for example, site-directed mutagenesis, so that the site-specific amino acid residue in the protein encoded includes substitutions, deletions, insertions, or additions.

Moreover, the protein variant encoded by the cynT, cynS, cynX and cynR may have a homology of not less than, for example, 80%, not less than 90%, for example, and not less than 95%, for example, with respect to the entire amino acid sequences shown in SEQ ID NO. 2, 4, 6 and 8 respectively as long as the activity of the CynT, CynS, CynX and CynR proteins prior to inactivation is maintained.

Activity of carbonic anhydrase, cyanase and cyanate MFS transporter can be measured by the method described in Guilloton M. B. et. al., (J. Biol. Chem.; 267(6):3731-4 (1992)), and Guilloton M. B. et. al., (J. Bacteriol.; 175(5):1443-51 (1993)).

Positive regulation of the cynTSX operon and the negative autoregulation of the cynR gene by the dual transcriptional regulator CynR can be assessed by the method described in (Sung Y.-C. et al., J. Bacteriol.; 174(11):3645-3650 (1992)).

Moreover, any of the cynT, cynS, cynX and cynR genes may be a variant which hybridizes with the nucleotide sequence shown in SEQ ID NO: 1, 3, 5 and 7, respectively, or a probe which can be prepared from the nucleotide sequences under stringent conditions. "Stringent conditions" include those under which a specific hybrid, for example, a hybrid having homology of not less than 60%, in another example, not less than 70%, and in another example, not less than 80%, and in another example, not less than 90%, and in another example, not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, for example, or 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, and is usually 100 bp to 1 kbp.

Homology between two amino acid sequences can be determined using the well-known methods, for example, the computer program BLAST 2.0.

Expression of the cynT, cynS, cynX and cynR genes can be attenuated by introducing a mutation into these genes on the chromosome so that the intracellular amount of the CynT, CynS, CynX and CynR proteins encoded by these genes is decreased as compared to an unmodified strain. Such a mutation can be introduction or insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the cynT, cynS, cynX and cynR genes can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and the bacterium to be modified is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. Nos. 6,303,383 and 5,616,480). Furthermore, the incorporation of a site-specific mutation by gene substitution using homologous recombination such as set forth above can also be conducted with a plasmid lacking the ability to replicate in the host.

Expression of the gene can also be attenuated by insertion of a transposon or an IS factor into the coding region of the gene (U.S. Pat. No. 5,175,107), or by conventional methods, such as mutagenesis treatment with UV irradiation or nitrosoguanidine (N-methyl-N'-nitro-N-nitrosoguanidine).

The delta cynT chromosomal mutant expresses an active cyanase but no active carbonic anhydrase. In contrast to the wild-type strain, the growth of the delta cynT strain is inhibited by cyanate, and the mutant strain is unable to degrade cyanate and therefore cannot use cyanate as the sole nitrogen source when grown at a partial $CO_2$ pressures ($pCO_2$) of 0.03% (air).

The delta cynS chromosomal mutant expresses an active carbonic anhydrase but no active cyanase. The delta cynS strain has sensitivity to cyanase activity to a lesser extent than delta cynT chromosomal mutant. A major physiological effect of cyanate on growth is inhibition of carbamoyl phosphate synthetase, which catalyze first step in both arginine and pyrimidine biosynthesis. So the addition of arginine plus uracil significantly relieves inhibition by cyanate for both the delta cynS chromosomal mutant and wild-type strains but not for the delta cynT chromosomal mutant because depletion of bicarbonate in the delta cynT chromosomal mutant strain with induced cyanase activity at low $pCO_2$ is more serious than the direct inhibitory effect of cyanate on growth.

No change in the phenotype compared with the parental strain was observed in the delta cynX chromosomal mutant except for slightly reduced levels of expression of cyanase by the mutant strains. This effect may be related to effects on the rates of transcription or on the stability of the transcript.

The chromosomal mutant with double mutation delta cynTSX and delta galk, and plasmids containing an insert with the cynR-galK transcriptional fusion sequence, expresses GalK activity when cyanate is present.

Therefore, the reduced or absent activity of the CynT, CynS, CynX and CynR proteins in the bacterium can be determined when compared to the parent unmodified bacterium. The presence or absence of the cynT, cynS, cynX and cynR genes in the chromosome of a bacterium can also be detected by well-known methods, including PCR, Southern blotting and the like. In addition, the level of gene expression can be estimated by measuring the amount of the RNA transcribed from the gene using various well-known methods, including Northern blotting, quantitative RT-PCR, and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-amino Acid-producing Bacteria

The bacterium which is modified to attenuate expression of the cynT, cynS, cynX or cynR gene may be a bacterium which is able to produce either an aromatic or a non-aromatic L-amino acids.

The bacterium can be obtained by attenuating expression of the cynT, cynS, cynX or cynR genes in a bacterium which inherently has the ability to produce L-amino acids. Alternatively, the bacterium can be obtained by imparting the ability to produce L-amino acids to a bacterium already having attenuated expression of the cynT, cynS, cynX or cynR gene.

L-threonine-producing Bacteria

Examples of parent strains which can be used to derive L-threonine-producing bacteria include, but are not limited to, strains belonging to the genus *Escherichia*, such as *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939, 307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene in this strain has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (Russia, 117545 Moscow, 1$^{st}$ Dorozhny proezd, 1) on Apr. 7, 1987 under the accession number VKPM B-3996.

*E. coli* VKPM B-5318 (EP 0593792B) also may be used as a parent strain to derive L-threonine-producing bacteria. The strain B-5318 is prototrophic with regard to isoleucine, and a temperature-sensitive lambda-phage C1 repressor and PR promoter replaces the regulatory region of the threonine operon in the plasmid pVIC40 harbored by the strain. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes:
the mutant thrA gene which codes for aspartokinase homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from the well-known plasmid pVIC40 which is presented in the threonine producing *E. coli* strain VKPM B-3996. Plasmid pVIC40 is described in detail in U.S. Pat. No. 5,705,371.

The rhtA gene is located at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181), and is located between the pexB and ompX genes. The DNA sequence expressing a protein encoded by the ORF1 has been designated the rhtA gene (rht: resistance to homoserine and threonine). Also, it is known that the rhtA23 mutation is an A-for-G substitution at position-1 with respect to the ATG start codon (ABSTRACTS of the 17$^{th}$ International Congress of Biochemistry and Molecular Biology in conjugation with the Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-lysine-producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenese (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme (WO2005/010175).

L-cysteine-producing Bacteria

Examples of parent strains which can be used to derive L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 which over-expresses genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO 0127307A1), and the like.

L-leucine-producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5, 5-trifluoroleucine (JP 62-34397 B and JP 8-70879 A); *E. coli* strains obtained by the genetic engineering methods such as those described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase which is not subject to feedback inhibition by L-leucine (U.S. Pat. No. 6,403,342). In addition, the bacterium may be improved by enhancing the expression of one or more genes coding for proteins which excrete L-amino acid from the bacterial cell. Examples of such genes include the b2682 and b2683 genes (ygaZH genes) (EP 1239041 A2).

L-histidine-producing Bacteria

Examples of parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554), and the like.

Examples of parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation into any of these genes which imparts resistance to the feedback inhibition to enzymes encoded by these genes (Russian Patent Nos. 2003677 and 2119536).

Specific examples of strains having an L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, which encoes an amino acid-exporter (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-glutamic Acid-producing Bacteria

Examples of parent strains which can be used to derive L-glutamic acid-producing bacteria include, but are not limited to, strains belonging to the genus *Escherichia*, such as *E. coli* VL334thrC⁺ (EP 1172433). *E. coli* VL334 (VKPM B-1641) is an L-isoleucine and L-threonine auxotrophic strain having mutations in the thrC and ilvA genes (U.S. Pat. No. 4,278,765). A wild-type allele of the thrC gene was transferred using general transduction with a bacteriophage P1 which was grown on the wild-type *E. coli* strain K12 (VKPM B-7) cells. As a result, an L-isoleucine auxotrophic strain VL334thrC⁺ (VKPM B-8961), which is able to produce L-glutamic acid, was obtained.

Examples of parent strains which can be used to derive the L-glutamic acid-producing bacteria include, but are not limited to, strains which are deficient in α-ketoglutarate dehydrogenase activity, or strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains which have been modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::$Km^R$
*E. coli* AJ12624 (FERM BP-3853)
*E. coli* AJ12628 (FERM BP-3854)
*E. coli* AJ12949 (FERM BP-4881)

*E. coli* W3110sucA::$Km^R$ is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FERM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the α-KGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depositary as *Enterobacter agglomerans*, for the purposes of this specification, they are described as *Pantoea ananatis*.

L-phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) may be used (EP 488-424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-tryptophan-producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) which is deficient in tryptophanyl-tRNA synthetase encoded by mutant trpS gene (U.S. Pat. No. 5,756,345); *E. coli* SV164 (pGH5) having a serA allele encoding phosphoglycerate dehydrogenase which is not subject to feedback inhibition by serine and a trpE allele encoding anthranilate synthase which is not subject to feedback inhibition by tryptophan (U.S. Pat. No. 6,180,373), *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO9708333, U.S. Pat. No. 6,319,696), and the like. L-tryptophan-producing bacteria belonging to the genus *Escherichia* which have enhanced activity of the protein encoded by the yedA or the yddG genes may also be used (U.S. patent applications 2003/0148473 A1 and 2003/0157667 A1).

Examples of parent strains which can be used to derive the L-tryptophan-producing bacteria also include strains in which one or more activities are enhanced of the following enzymes: anthranilate synthase (trpE), phosphoglycerate dehydrogenase (serA), and tryptophan synthase (trpAB). The anthranilate synthase and phosphoglycerate dehydrogenase are both subject to feedback inhibition by L-tryptophan and L-serine, therefore a mutation desensitizing the feedback inhibition may be introduced into these enzymes. Specific examples of strains having such a mutation include *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria also include strains which have been transformed with the tryptophan operon containing a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). Tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-proline-producing Bacteria

Examples of parent strains which can be used to deriving L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes include the proB gene coding for glutamate kinase which is desensitized to feedback inhibition by L-proline (DE Patent 3127361). In addition, the bacterium may be improved by enhancing the expression of one or more genes coding for proteins responsible for secreting L-amino acids from the bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-arginine-producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application 2002/058315 A1) and derivative strains thereof harboring mutant N-acetylglutamate synthase (Russian Patent Application No. 2001112869), *E. coli* strain 382 (VKPM B-7926) (EP 1170358A1), an arginine-producing strain transformed with the argA gene encoding N-acetylglutamate synthetase (EP1170361A1), and the like.

Examples of parent strains which can be used to derive L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), carbamoyl phosphate synthetase (carAB), and so forth.

L-valine-producing Bacteria

Example of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon responsible for attenuation so that the produced L-valine cannot attenuate expression of the operon. Furthermore, the ilvA gene in the operon is desirably disrupted so that threonine deaminase activity is decreased.

Examples of parent strains which can be used to derive L-valine-producing bacteria also include mutants of aminoacyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-isoleucine-producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

Exemplary methods of the present invention include producing an L-amino acid by cultivating the bacterium as described above in a culture medium to produce and secrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

The chosen culture medium may be either a synthetic or natural medium, so long as it includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated CynT Gene

1. Deletion of the CynT Gene.

The cynT gene was deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers P1 (SEQ ID NO: 9) and P2 (SEQ ID NO: 10), which are complementary to both the region adjacent to the cynT gene and the gene conferring antibiotic resistance, respectively, in the template plasmid, were constructed. The plasmid pACYC184 (NBL Gene Sciences Ltd., UK) (GenBank/EMBL accession number X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1152 bp PCR product (FIG. 1) was obtained and purified in agarose gel and used for electroporation of E. coli MG1655 (ATCC 700926), which contains the plasmid pKD46. The plasmid pKD46 (Datsenko, K. A. and Wanner, B. L., Proc. Natl. Acad. Sci. USA, 2000, 97:12:6640-45) contains a temperature-sensitive replication origin, and includes a 2,154 nucleotide (31088-33241) DNA fragment of phage λ (GenBank accession No. J02459), as well as the genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, U.S.A.).

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 μl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 hours and were then plated onto L-agar containing chloramphenicol (30 μg/ml) and grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the CynT Gene Deletion by PCR.

Figure 2:
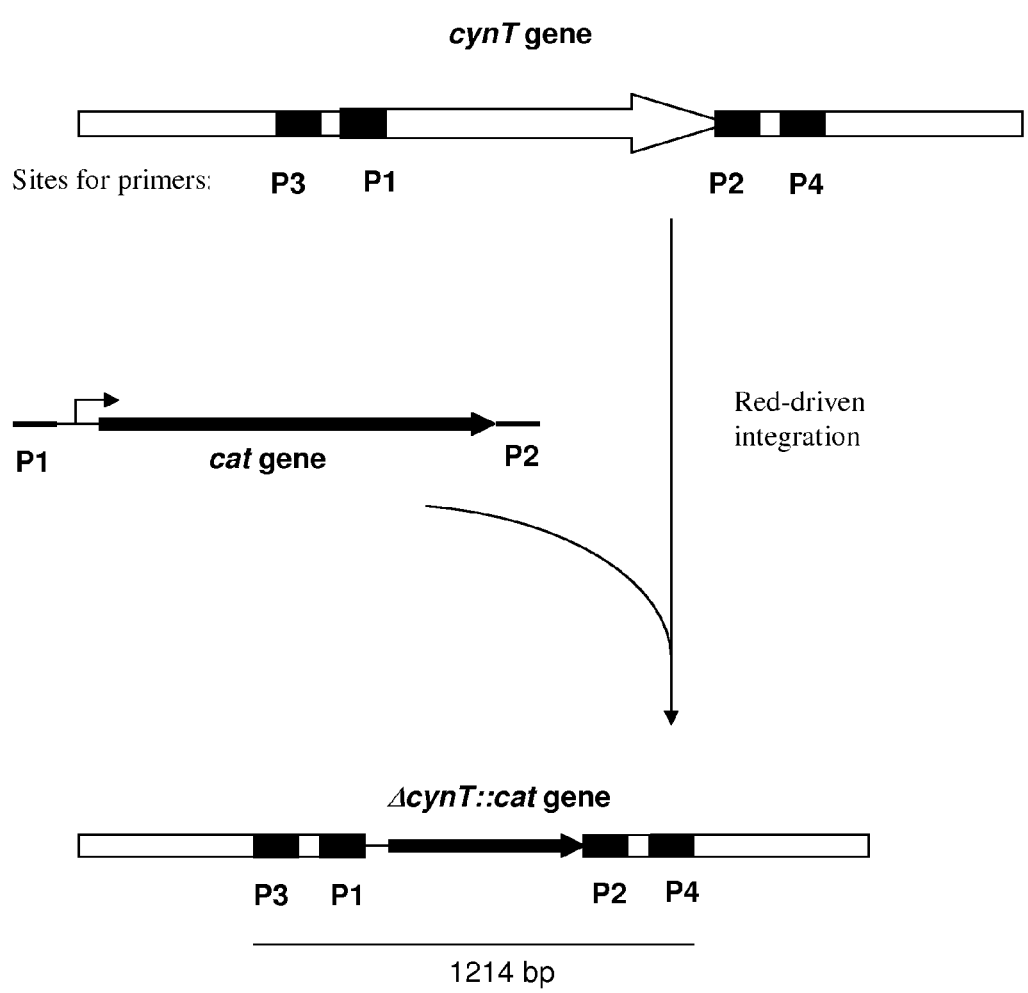
FIG. 2 shows the construction of the chromosomal DNA fragment including the inactivated cynT gene.

The mutants in which the cynT gene is deleted, and which are marked with the Cm resistance gene, were verified by PCR. Locus-specific primers P3 (SEQ ID NO: 11) and P4 (SEQ ID NO: 12) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained using parental $cynT^+$ strain MG1655 as the template is 792 bp in length. The PCR product obtained using the mutant strain as the template is 1214 nucleotides in length (FIG. 2). The mutant strain was named MG1655 ΔcynT::cat.

Example 2

Production of L-threonine by E. coli Strain B-3996-ΔCynT

To test the effect of inactivation of the cynT gene on threonine production, DNA fragments from the chromosome of the above-described E. coli MG1655 ΔcynT::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain B-3996ΔcynT. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1 Dorozhny proezd, 1) under the accession number VKPM B-3996.

Both E. coli strains, B-3996 and B-3996-ΔcynT, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium was determined by paper chromatography using the following mobile phase: butanol-acetic acid-water=4:1:1 (v/v). A solution of ninhydrin (2%) in acetone was used as a visualizing reagent. A spot containing L-threonine was cut out, the L-threonine was eluted with 0.5% water solution of $CdCl_2$, and the amount of L-threonine was estimated spectrophotometrically at 540 nm. The results of eight independent test tube fermentations are shown in Table 1. As follows from Table 1, B-3996-ΔcynT produced a higher amount of L-threonine, as compared with B-3996.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0.

TABLE 1

| Strain | OD$_{540}$ | Amount of L-threonine, g/l |
|---|---|---|
| B-3996 | 23.7 ± 0.8 | 25.8 ± 0.3 |
| B-3996-ΔcynT | 21.8 ± 1.2 | 26.7 ± 0.6 |

Hereinafter, the geneX mentioned in the Examples described below means the cynT gene, cynS gene, cynX gene, cynR gene, or combinations of thereof, including the cynTSX operon, cynTSX operon plus cynR gene.

Example 3

Construction of a Strain with an Inactivated geneX

1. Deletion of the geneX.

The geneX can be deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers, which are complementary to both the region adjacent to the geneX and the gene conferring antibiotic resistance in the template plasmid, respectively, can be constructed similar to Example 1 (FIG. 1). The plasmid pACYC184 (NBL Gene Sciences Ltd., UK) (GenBank/EMBL accession number X06403) can be used as the template in the PCR reaction. Conditions for PCR can be as described in the Example 1.

The PCR product can be obtained and purified in agarose gel and used for electroporation of *E. coli* MG1655 (ATCC 700926), which contains the plasmid pKD46 which contains a temperature-sensitive replication origin. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible P$_{araB}$ promoter. The plasmid pKD46 is necessary for integration of the PCR product into the chromosome of strain MG1655.

Electrocompetent cells can be prepared and electroporation can be performed as described in the Example 1. Cells after electroporation can be incubated with 1 ml of SOC medium (Sambrook et al, "Molecular Cloning A Laboratory Manual, Second Edition", Cold Spring Harbor Laboratory Press (1989)) at 37° C. for 2.5 hours and can be then plated onto L-agar containing chloramphenicol (30 μg/ml) and grown at 37° C. to select Cm$^R$ recombinants. Then, to eliminate the pKD46 plasmid, 2 passages on L-agar with Cm at 42° C. can be performed and the obtained colonies can be tested for sensitivity to ampicillin.

2. Verification of the geneX Deletion by PCR.

The mutants in which the geneX is deleted, and which are marked with the Cm resistance gene, can be verified by PCR. Locus-specific primers can be used in PCR for verification. Conditions for PCR verification can be as described in the Example 1. The PCR product obtained using the parental X$^+$ strain MG1655 as the template, must be longer in length then the PCR product obtained using the mutant strain as the template. The mutant strain can be named MG1655 ΔgeneX::cat.

Example 4

Production of L-threonine by *E. coli* Strain B-3996-ΔgeneX

To test the effect of inactivation of the geneX on threonine production, DNA fragments from the chromosome of the above-described *E. coli* MG1655 ΔgeneX::cat can be transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain B-3996ΔX.

Both *E. coli* strains, B-3996 and B-3996-ΔgeneX, can be grown as described in Example 2.

After cultivation, the amount of L-threonine which had accumulated in the medium can be determined by paper as described in Example 2.

Example 5

Production of L-lysine by *E. coli* Strain AJ11442-ΔgeneX

To test the effect of inactivation of the geneX on lysine production, DNA fragments from the chromosome of the above-described *E. coli* strain MG1655 ΔX::cat can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain the strain AJ11442-ΔgeneX. The strain AJ14442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both *E. coli* strains, AJ11442 and AJ11442-ΔgeneX, can be cultured in L-medium at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm.

After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| (NH$_4$)$_2$SO$_4$ | 24 |
| K$_2$HPO$_4$ | 1.0 |
| MgSO$_4$•7H$_2$O | 1.0 |
| FeSO$_4$•7H$_2$O | 0.01 |
| MnSO$_4$•5H$_2$O | 0.01 |
| Yeast extract | 2.0 |

The pH is adjusted to 7.0 by KOH and the medium is autoclaved at 115° C. for 10 min. Glucose and MgSO$_4$.7H$_2$O are sterilized separately. CaCO$_3$ is dry-heat sterilized at 180° C. for 2 hours and added to the medium for a final concentration of 30 g/l.

Example 6

Production of L-cysteine by *E. coli* Strain JM15(ydeD)-ΔgeneX

To test the effect of inactivation of the gene X on L-cysteine production, DNA fragments from the chromosome of the above-described *E. coli* MG1655 ΔgeneX::cat can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-ΔgeneX.

*E. coli* strain JM15(ydeD) is a derivative of *E. coli* strain JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663). The strain JM15 (CGSC #5042) can be obtained from The Coli Genetic Stock Collection at the *E. coli* Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 7

Production of L-leucine by *E. coli* 57-ΔgeneX

To test the effect of inactivation of the gene X on L-leucine production, DNA fragments from the chromosome of the above-described *E. coli* strain MG1655 ΔgeneX::cat can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-pMW-ΔX. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains, 57 and 57-ΔgeneX can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 8

Production of L-histidine by *E. coli* Strain 80-ΔgeneX

To test the effect of inactivation of the gene X on L-histidine production, DNA fragments from the chromosome of the above-described *E. coli* MG1655 ΔgeneX::cat can be transferred to the histidine-producing *E. coli* strain 80 by P1 transduction (Miller, J. H. Experiments in Molecular Genetics, Cold Spring Harbor Lab. Press, 1972, Plainview, N.Y.) to obtain strain 80-ΔgeneX. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both *E. coli* strains, 80 and 80-ΔgeneX, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 9

Production of L-glutamate by *E. coli* Strain VL334thrC$^+$-ΔgeneX

To test the effect of inactivation of the gene X on L-glutamate production, DNA fragments from the chromosome of the above-described *E. coli* strain MG1655 ΔgeneX::cat can be transferred to the *E. coli* L-glutamate-producing strain VL334thrC$^+$ (EP 1172433) by P1 transduction (Miller, J. H. Experiments in Molecular Genetics, Cold Spring Harbor Lab. Press, 1972, Plainview, N.Y.) to obtain the strain VL334thrC$^+$-ΔgeneX. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC$^+$ and VL334thrC$^+$-ΔgeneX, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), $KH_2PO_4$ (2 g/l), $MgSO_4$ (1 g/l), thiamine (0.1 mg/ml), L-isoleucine (70 μg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 10

Production of L-phenylalanine by E. coli Strain AJ12739-ΔgeneX

To test the effect of inactivation of the gene X on L-phenylalanine production, DNA fragments from the chromosome of the above-described E. coli MG1655 ΔgeneX::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain strain AJ12739-ΔgeneX. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Both strains, AJ12739-ΔgeneX and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4·7H_2O$ | 1.0 |
| $FeSO_4·7H_2O$ | 0.01 |
| $MnSO_4·5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 11

Production of L-tryptophan by E. coli Strain SV164 (pGH5)-ΔgeneX

To test the effect of inactivation of the gene X on L-tryptophan production, DNA fragments from the chromosome of the above-described E. coli strain MG1655 ΔX::cat can be transferred to the tryptophan-producing E. coli strain SV164 (pGH5) by P1 transduction (Miller, J. H. Experiments in Molecular Genetics, Cold Spring Harbor Lab. Press, 1972, Plainview, N.Y.) to obtain the strain SV164(pGH5)-ΔgeneX. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143.

Both strains, SV164(pGH5)-ΔgeneX and SV164(pGH5), can each be cultivated with shaking at 32° C. for 18 hours in 3 ml of nutrient broth supplemented with tetracycline (10 mg/l, marker of pGH5 plasmid). The obtained cultures (0.3 ml each) can be inoculated into 3 ml of a fermentation medium containing tetracycline (10 mg/l) in 20×200-mm test tubes, and cultivated at 32° C. for 72 hours with a rotary shaker at 250 rpm. After cultivation, the amount of tryptophan which accumulates in the medium can be determined by TLC as described in Example 10.

The fermentation medium components are listed in Table 2, but should be sterilized in separate groups (A, B, C, D, E, F, and G), as shown, to avoid adverse interactions during sterilization.

TABLE 2

| Solutions | Component | Final concentration, g/l |
|---|---|---|
| A | $KH_2PO_4$ | 0.28 |
| | NaCl | 0.14 |
| | $(NH_4)_2SO_4$ | 16 |
| | L-Methionine | 0.08 |
| | L-Phenylalanine | 0.28 |
| | L-Tyrosine | 0.28 |
| | Mameno (total N) | 0.07 |
| B | Glucose | 40.0 |
| | $MgSO_4·7H_2O$ | 0.03 |
| C | $FeSO_4·7H_2O$ | 0.03 |
| D | $Na_2MoO_4·2H_2O$ | 0.00015 |
| | $H_3BO_3$ | 0.0025 |
| | $CoCl_2·6H_2O$ | 0.00007 |
| | $CuSO_4·5H_2O$ | 0.00025 |
| | $MnCl_2·4H_2O$ | 0.0016 |
| | $ZnSO_4·7H_2O$ | 0.0003 |
| E | Thiamine HCl | 0.001 |
| F | $CaCO_3$ | 30.0 |
| G | Pyridoxine | 0.03 |

The pH of solution A is adjusted to 7.1 with $NH_4OH$.

Example 12

Production of L-proline by E. coli Strain 702ilvA-ΔgeneX

To test the effect of inactivation of the gene X on L-proline production, DNA fragments from the chromosome of the above-described E. coli strain MG1655 ΔgeneX::cat can be transferred to the proline-producing E. coli strain 702ilvA by P1 transduction (Miller, J. H. Experiments in Molecular Genetics, Cold Spring Harbor Lab. Press, 1972, Plainview, N.Y.) to obtain strain 702ilvA-ΔgeneX. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains, 702ilvA and 702ilvA-ΔgeneX, can be grown for 18-24 hours at 37° C. on L-agar plates. Then, these strains can be cultivated under the same conditions as in Example 9.

Example 13

Production of L-arginine by E. coli Strain 382-ΔgeneX

To test the effect of inactivation of the gene X on L-arginine production, DNA fragments from the chromosome of the above-described E. coli strain MG1655 ΔX::cat can be transferred to the arginine-producing E. coli strain 382 by P1 transduction (Miller, J. H. Experiments in Molecular Genetics, Cold Spring Harbor Lab. Press, 1972, Plainview, N.Y.) to obtain strain 382-ΔgeneX. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382-ΔgeneX and 382, can be cultivated with shaking at 37° C. for 18 hours in 3 ml of nutrient broth, and 0.3 ml of the obtained cultures can be inoculated into 2 ml of a fermentation medium in 20×200-mm test tubes and cultivated at 32° C. for 48 hours on a rotary shaker.

After the cultivation, the amount of L-arginine which had accumulates in the medium can be determined by paper chromatography using the following mobile phase: butanol:acetic acid:water=4:1:1 (v/v). A solution of ninhydrin (2%) in acetone can be used as a visualizing reagent. A spot containing L-arginine can be cut out, the L-arginine can be eluted with 0.5% water solution of $CdCl_2$, and the amount of L-arginine can be estimated spectrophotometrically at 540 nm.

The composition of the fermentation medium (g/l) is as follows:

| | |
|---|---|
| Glucose | 48.0 |
| (NH4)$_2$SO$_4$ | 35.0 |
| KH$_2$PO$_4$ | 2.0 |
| MgSO$_4$·7H$_2$O | 1.0 |
| Thiamine HCl | 0.0002 |
| Yeast extract | 1.0 |
| L-isoleucine | 0.1 |
| CaCO$_3$ | 5.0 |

Glucose and magnesium sulfate are sterilized separately. CaCO$_3$ is dry-heat sterilized at 180° C. for 2 hours. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of an L-amino acid by a bacterium of the Enterobacteriaceae family can be enhanced.

The invention claimed is:

1. A method for producing an L-amino acid comprising:
   A)—cultivating an L-amino acid-producing *Escherichia coli* in a medium, wherein said *Escherichia* coli has been modified to attenuate expression of a gene on the chromosome of said *Escherichia coli* selected from the group consisting of cynT, cynR, and combinations thereof, and
   (B)—collecting said L-amino acid from the medium,
   wherein said L-amino acid is selected from the group consisting of L-threonine, L-isoleucine, L-lysine, and L-methionine.

2. The method according to claim 1, wherein said expression is attenuated by inactivation of the gene(s).

3. The method according to claim 1, wherein said L-amino acid is L-threonine.

* * * * *

SEQUENCE LISTING

```
<160> NUMBER OF SEQ ID NOS: 12

<210> SEQ ID NO 1
<211> LENGTH: 660
<212> TYPE: DNA
<213> ORGANISM: Escherichia coli
<220> FEATURE:
<221> NAME/KEY: CDS
<222> LOCATION: (1)..(660)
<223> OTHER INFORMATION: cynT

<400> SEQUENCE: 1 gtg aaa gag att att gat gga ttc ctt aaa ttc cag cgc gag gca ttt      48
Val Lys Glu Ile Ile Asp Gly Phe Leu Lys Phe Gln Arg Glu Ala Phe
1               5                   10                  15 ccg aag cgg gaa gcc ttg ttt aaa cag ctg gcg aca cag caa agc ccg      96
Pro Lys Arg Glu Ala Leu Phe Lys Gln Leu Ala Thr Gln Gln Ser Pro
                20                  25                  30 cgc aca ctt ttt atc tcc tgc tcc gac agc cgt ctg gtc cct gag ctg     144
Arg Thr Leu Phe Ile Ser Cys Ser Asp Ser Arg Leu Val Pro Glu Leu
            35                  40                  45 gtg acg caa cgt gag cct ggc gat ctg ttc gtt att cgc aac gcg ggc     192
Val Thr Gln Arg Glu Pro Gly Asp Leu Phe Val Ile Arg Asn Ala Gly
        50                  55                  60 aat atc gtc cct tcc tac ggg ccg gaa ccc ggt ggc gtt tct gct tcg     240
Asn Ile Val Pro Ser Tyr Gly Pro Glu Pro Gly Gly Val Ser Ala Ser
65                  70                  75                  80 gtg gag tat gcc gtc gct gcg ctt cgg gta tct gac att gtg att tgt     288
Val Glu Tyr Ala Val Ala Ala Leu Arg Val Ser Asp Ile Val Ile Cys
                85                  90                  95 ggt cat tcc aac tgt ggc gcg atg acc gcc att gcc agc tgt cag tgc     336
Gly His Ser Asn Cys Gly Ala Met Thr Ala Ile Ala Ser Cys Gln Cys
            100                 105                 110 atg gac cat atg cct gcc gtc tcc cac tgg ctg cgt tat gcc gat tca     384
Met Asp His Met Pro Ala Val Ser His Trp Leu Arg Tyr Ala Asp Ser
```

-continued

```
                 115                 120                 125
gcc cgc gtc gtt aat gag gcg cgc ccg cat tcc gat tta ccg tca aaa      432
Ala Arg Val Val Asn Glu Ala Arg Pro His Ser Asp Leu Pro Ser Lys
130                 135                 140 gct gcg gcg atg gta cgt gaa aac gtc att gct cag ttg gct aat ttg      480
Ala Ala Ala Met Val Arg Glu Asn Val Ile Ala Gln Leu Ala Asn Leu
145                 150                 155                 160 caa act cat cca tcg gtg cgc ctg gcg ctc gaa gag ggg cgg atc gcc      528
Gln Thr His Pro Ser Val Arg Leu Ala Leu Glu Glu Gly Arg Ile Ala
                165                 170                 175 ctg cac ggc tgg gtc tac gac att gaa agc ggc agc atc gca gct ttt      576
Leu His Gly Trp Val Tyr Asp Ile Glu Ser Gly Ser Ile Ala Ala Phe
                180                 185                 190 gac ggc gca acc cgc cag ttt gtg cca ctg gcc gct aat cct cgc gtt      624
Asp Gly Ala Thr Arg Gln Phe Val Pro Leu Ala Ala Asn Pro Arg Val
    195                 200                 205 tgt gcc ata ccg cta cgc caa ccg acc gca gcg taa                      660
Cys Ala Ile Pro Leu Arg Gln Pro Thr Ala Ala
    210                 215

<210> SEQ ID NO 2
<211> LENGTH: 219
<212> TYPE: PRT
<213> ORGANISM: Escherichia coli

<400> SEQUENCE: 2

Val Lys Glu Ile Ile Asp Gly Phe Leu Lys Phe Gln Arg Glu Ala Phe
1               5                   10                  15

Pro Lys Arg Glu Ala Leu Phe Lys Gln Leu Ala Thr Gln Ser Pro
            20                  25                  30

Arg Thr Leu Phe Ile Ser Cys Ser Asp Ser Arg Leu Val Pro Glu Leu
            35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Ala Leu Arg Val Ser Asp Ile Val Ile Cys
                85                  90                  95

Gly His Ser Asn Cys Gly Ala Met Thr Ala Ile Ala Ser Cys Gln Cys
            100                 105                 110

Met Asp His Met Pro Ala Val Ser His Trp Leu Arg Tyr Ala Asp Ser
        115                 120                 125

Ala Arg Val Val Asn Glu Ala Arg Pro His Ser Asp Leu Pro Ser Lys
130                 135                 140

Ala Ala Ala Met Val Arg Glu Asn Val Ile Ala Gln Leu Ala Asn Leu
145                 150                 155                 160

Gln Thr His Pro Ser Val Arg Leu Ala Leu Glu Glu Gly Arg Ile Ala
                165                 170                 175

Leu His Gly Trp Val Tyr Asp Ile Glu Ser Gly Ser Ile Ala Ala Phe
                180                 185                 190

Asp Gly Ala Thr Arg Gln Phe Val Pro Leu Ala Ala Asn Pro Arg Val
    195                 200                 205

Cys Ala Ile Pro Leu Arg Gln Pro Thr Ala Ala
    210                 215

<210> SEQ ID NO 3
<211> LENGTH: 471
<212> TYPE: DNA
```

<213> ORGANISM: Escherichia coli
<220> FEATURE:
<221> NAME/KEY: CDS
<222> LOCATION: (1)..(471)
<223> OTHER INFORMATION: cynS

<400> SEQUENCE: 3

```
atg att cag tca caa att aac cgc aat att cgt ctt gat ctt gcc gat        48
Met Ile Gln Ser Gln Ile Asn Arg Asn Ile Arg Leu Asp Leu Ala Asp
1               5                   10                  15 gcc att ttg ctc agc aaa gct aaa aaa gat ctc tca ttt gcc gag att        96
Ala Ile Leu Leu Ser Lys Ala Lys Lys Asp Leu Ser Phe Ala Glu Ile
                20                  25                  30 gcc gac ggc acc ggt ctg gca gaa gcc ttt gta acc gcg gct ttg ctg       144
Ala Asp Gly Thr Gly Leu Ala Glu Ala Phe Val Thr Ala Ala Leu Leu
            35                  40                  45 ggt cag cag gcg ctt cct gcc gac gcc gcc cgc ctg gtc ggg gcg aag       192
Gly Gln Gln Ala Leu Pro Ala Asp Ala Ala Arg Leu Val Gly Ala Lys
        50                  55                  60 ctg gat ctc gac gaa gac tcc att cta ctg ttg cag atg att cca ctg       240
Leu Asp Leu Asp Glu Asp Ser Ile Leu Leu Leu Gln Met Ile Pro Leu
65                  70                  75                  80 cgt ggc tgc att gat gac cgt att cca act gac cca acg atg tat cgt       288
Arg Gly Cys Ile Asp Asp Arg Ile Pro Thr Asp Pro Thr Met Tyr Arg
                85                  90                  95 ttc tat gaa atg ttg cag gtg tac ggt aca acc ctg aaa gcg ttg gtt       336
Phe Tyr Glu Met Leu Gln Val Tyr Gly Thr Thr Leu Lys Ala Leu Val
                100                 105                 110 cat gag aaa ttt ggc gat ggc att att agc gcg att aac ttc aaa ctc       384
His Glu Lys Phe Gly Asp Gly Ile Ile Ser Ala Ile Asn Phe Lys Leu
            115                 120                 125 gac gtt aag aaa gtg gcg gac ccg gaa ggt ggc gaa cgt gcg gtc atc       432
Asp Val Lys Lys Val Ala Asp Pro Glu Gly Gly Glu Arg Ala Val Ile
        130                 135                 140 acc tta gat ggt aaa tat ctg ccg acc aaa ccg ttc tga               471
Thr Leu Asp Gly Lys Tyr Leu Pro Thr Lys Pro Phe
145                 150                 155
```

<210> SEQ ID NO 4
<211> LENGTH: 156
<212> TYPE: PRT
<213> ORGANISM: Escherichia coli

<400> SEQUENCE: 4

```
Met Ile Gln Ser Gln Ile Asn Arg Asn Ile Arg Leu Asp Leu Ala Asp
1               5                   10                  15

Ala Ile Leu Leu Ser Lys Ala Lys Lys Asp Leu Ser Phe Ala Glu Ile
                20                  25                  30

Ala Asp Gly Thr Gly Leu Ala Glu Ala Phe Val Thr Ala Ala Leu Leu
            35                  40                  45

Gly Gln Gln Ala Leu Pro Ala Asp Ala Ala Arg Leu Val Gly Ala Lys
        50                  55                  60

Leu Asp Leu Asp Glu Asp Ser Ile Leu Leu Leu Gln Met Ile Pro Leu
65                  70                  75                  80

Arg Gly Cys Ile Asp Asp Arg Ile Pro Thr Asp Pro Thr Met Tyr Arg
                85                  90                  95

Phe Tyr Glu Met Leu Gln Val Tyr Gly Thr Thr Leu Lys Ala Leu Val
                100                 105                 110

His Glu Lys Phe Gly Asp Gly Ile Ile Ser Ala Ile Asn Phe Lys Leu
            115                 120                 125
```

```
Asp Val Lys Lys Val Ala Asp Pro Glu Gly Gly Glu Arg Ala Val Ile
    130                 135                 140

Thr Leu Asp Gly Lys Tyr Leu Pro Thr Lys Pro Phe
145                 150                 155

<210> SEQ ID NO 5
<211> LENGTH: 1155
<212> TYPE: DNA
<213> ORGANISM: Escherichia coli
<220> FEATURE:
<221> NAME/KEY: CDS
<222> LOCATION: (1)..(1155)
<223> OTHER INFORMATION: cynX

<400> SEQUENCE: 5 atg ctg ctg gta ctg gtg ctg att ggt ctt aat atg cga cca ctg ctc      48
Met Leu Leu Val Leu Val Leu Ile Gly Leu Asn Met Arg Pro Leu Leu
1               5                   10                  15 acc tcc gtc ggg cca ctg cta ccg caa ttg cgc cag gcg agc gga atg      96
Thr Ser Val Gly Pro Leu Leu Pro Gln Leu Arg Gln Ala Ser Gly Met
            20                  25                  30 agc ttt agc gtg gct gcc ctg ttg acc gct ctg ccg gtg gtt acc atg     144
Ser Phe Ser Val Ala Ala Leu Leu Thr Ala Leu Pro Val Val Thr Met
        35                  40                  45 ggc ggg ctg gcg ctg gcc gga agc tgg ctt cat cag cat gtc agc gaa     192
Gly Gly Leu Ala Leu Ala Gly Ser Trp Leu His Gln His Val Ser Glu
    50                  55                  60 cgt cgc agt gtc gcc atc agt ctg ttg ctg att gcc gtc ggt gca ttg     240
Arg Arg Ser Val Ala Ile Ser Leu Leu Leu Ile Ala Val Gly Ala Leu
65                  70                  75                  80 atg cgt gag ctt tac ccg caa agt gcg ctg ctg ctt agc agc gca ctg     288
Met Arg Glu Leu Tyr Pro Gln Ser Ala Leu Leu Leu Ser Ser Ala Leu
                85                  90                  95 ctt ggt ggg gtg ggg atc ggc atc att cag gcg gtg atg cct tcg gtg     336
Leu Gly Gly Val Gly Ile Gly Ile Ile Gln Ala Val Met Pro Ser Val
            100                 105                 110 att aaa cgg cgg ttt cag cag cgc acg cca ctg gtg atg ggg ctg tgg     384
Ile Lys Arg Arg Phe Gln Gln Arg Thr Pro Leu Val Met Gly Leu Trp
        115                 120                 125 tcc gcg gct ctg atg ggc ggc ggt ggg ctt ggt gcc gcc ata acg ccc     432
Ser Ala Ala Leu Met Gly Gly Gly Gly Leu Gly Ala Ala Ile Thr Pro
    130                 135                 140 tgg tta gtt caa cat agc gaa acc tgg tat caa aca ctc gcc tgg tgg     480
Trp Leu Val Gln His Ser Glu Thr Trp Tyr Gln Thr Leu Ala Trp Trp
145                 150                 155                 160 gcg ctg cct gcc gtt gtt gcg ctc ttt gcc tgg tgg tgg caa agc gcc     528
Ala Leu Pro Ala Val Val Ala Leu Phe Ala Trp Trp Trp Gln Ser Ala
                165                 170                 175 cgc gag gtc gcc tct tcc cac aag aca aca acc act ccg gtt cgc gtg     576
Arg Glu Val Ala Ser Ser His Lys Thr Thr Thr Thr Pro Val Arg Val
            180                 185                 190 gta ttc act ccc cgc gcg tgg acg ctg ggt gtt tac ttc ggt ctg att     624
Val Phe Thr Pro Arg Ala Trp Thr Leu Gly Val Tyr Phe Gly Leu Ile
        195                 200                 205 aac ggc ggt tac gcc agc ctg att gcc tgg tta ccc gct ttc tat att     672
Asn Gly Gly Tyr Ala Ser Leu Ile Ala Trp Leu Pro Ala Phe Tyr Ile
    210                 215                 220 gag att ggt gcc agc gcg cag tac agc ggt tcc tta ctg gca ttg atg     720
Glu Ile Gly Ala Ser Ala Gln Tyr Ser Gly Ser Leu Leu Ala Leu Met
225                 230                 235                 240 acg ctt ggg caa gcc gca gga gct ttg ctg atg cct gct atg gct cgc     768
Thr Leu Gly Gln Ala Ala Gly Ala Leu Leu Met Pro Ala Met Ala Arg
```

```
cat cag gat cgg cgc aaa ctg tta atg ctg gcg ctg gtg tta caa ctg    816
His Gln Asp Arg Arg Lys Leu Leu Met Leu Ala Leu Val Leu Gln Leu
            260                 265                 270 gtg ggg ttc tgc ggc ttt atc tgg ctg ccg atg caa ttg ccg gta ttg    864
Val Gly Phe Cys Gly Phe Ile Trp Leu Pro Met Gln Leu Pro Val Leu
                275                 280                 285 tgg gcg atg gtg tgt ggg tta ggt ctg ggc ggc gcg ttt ccg ctc tgt    912
Trp Ala Met Val Cys Gly Leu Gly Leu Gly Gly Ala Phe Pro Leu Cys
        290                 295                 300 ttg ctg ctg gcg ctc gat cac tct gtg caa ccg gct att gct ggc aag    960
Leu Leu Leu Ala Leu Asp His Ser Val Gln Pro Ala Ile Ala Gly Lys
305                 310                 315                 320 ctg gtg gcg ttt atg cag gga atc ggt ttt atc atc gcc ggg ctt gcc   1008
Leu Val Ala Phe Met Gln Gly Ile Gly Phe Ile Ile Ala Gly Leu Ala
                325                 330                 335 ccg tgg ttt tct ggc gtg ctg cgt agt atc agc ggc aat tac ctg atg   1056
Pro Trp Phe Ser Gly Val Leu Arg Ser Ile Ser Gly Asn Tyr Leu Met
            340                 345                 350 gac tgg gca ttt cat gcg ctg tgc gtc gtt ggg ctg atg atc ata acc   1104
Asp Trp Ala Phe His Ala Leu Cys Val Val Gly Leu Met Ile Ile Thr
        355                 360                 365 ctg cgt ttt gca cca gta cgt ttt ccg cag ctg tgg gtc aaa gag gca   1152
Leu Arg Phe Ala Pro Val Arg Phe Pro Gln Leu Trp Val Lys Glu Ala
370                 375                 380 tga                                                                1155

<210> SEQ ID NO 6
<211> LENGTH: 384
<212> TYPE: PRT
<213> ORGANISM: Escherichia coli

<400> SEQUENCE: 6

Met Leu Leu Val Leu Val Leu Ile Gly Leu Asn Met Arg Pro Leu Leu
1               5                   10                  15

Thr Ser Val Gly Pro Leu Leu Pro Gln Leu Arg Gln Ala Ser Gly Met
            20                  25                  30

Ser Phe Ser Val Ala Ala Leu Leu Thr Ala Leu Pro Val Val Thr Met
        35                  40                  45

Gly Gly Leu Ala Leu Ala Gly Ser Trp Leu His Gln His Val Ser Glu
    50                  55                  60

Arg Arg Ser Val Ala Ile Ser Leu Leu Leu Ile Ala Val Gly Ala Leu
65                  70                  75                  80

Met Arg Glu Leu Tyr Pro Gln Ser Ala Leu Leu Leu Ser Ser Ala Leu
                85                  90                  95

Leu Gly Gly Val Gly Ile Gly Ile Ile Gln Ala Val Met Pro Ser Val
            100                 105                 110

Ile Lys Arg Arg Phe Gln Gln Arg Thr Pro Leu Val Met Gly Leu Trp
        115                 120                 125

Ser Ala Ala Leu Met Gly Gly Gly Leu Gly Ala Ala Ile Thr Pro
    130                 135                 140

Trp Leu Val Gln His Ser Glu Thr Trp Tyr Gln Thr Leu Ala Trp Trp
145                 150                 155                 160

Ala Leu Pro Ala Val Val Ala Leu Phe Ala Trp Trp Gln Ser Ala
                165                 170                 175

Arg Glu Val Ala Ser Ser His Lys Thr Thr Thr Pro Val Arg Val
            180                 185                 190
```

-continued

```
Val Phe Thr Pro Arg Ala Trp Thr Leu Gly Val Tyr Phe Gly Leu Ile
        195                 200                 205

Asn Gly Gly Tyr Ala Ser Leu Ile Ala Trp Leu Pro Ala Phe Tyr Ile
210                 215                 220

Glu Ile Gly Ala Ser Ala Gln Tyr Ser Gly Ser Leu Leu Ala Leu Met
225                 230                 235                 240

Thr Leu Gly Gln Ala Ala Gly Ala Leu Leu Met Pro Ala Met Ala Arg
                245                 250                 255

His Gln Asp Arg Arg Lys Leu Leu Met Leu Ala Leu Val Leu Gln Leu
                260                 265                 270

Val Gly Phe Cys Gly Phe Ile Trp Leu Pro Met Gln Leu Pro Val Leu
                275                 280                 285

Trp Ala Met Val Cys Gly Leu Gly Leu Gly Gly Ala Phe Pro Leu Cys
290                 295                 300

Leu Leu Leu Ala Leu Asp His Ser Val Gln Pro Ala Ile Ala Gly Lys
305                 310                 315                 320

Leu Val Ala Phe Met Gln Gly Ile Gly Phe Ile Ile Ala Gly Leu Ala
                325                 330                 335

Pro Trp Phe Ser Gly Val Leu Arg Ser Ile Ser Gly Asn Tyr Leu Met
                340                 345                 350

Asp Trp Ala Phe His Ala Leu Cys Val Val Gly Leu Met Ile Ile Thr
                355                 360                 365

Leu Arg Phe Ala Pro Val Arg Phe Pro Gln Leu Trp Val Lys Glu Ala
                370                 375                 380
```

<210> SEQ ID NO 7
<211> LENGTH: 900
<212> TYPE: DNA
<213> ORGANISM: Escherichia coli
<220> FEATURE:
<221> NAME/KEY: CDS
<222> LOCATION: (1)..(900)
<223> OTHER INFORMATION: cynR

<400> SEQUENCE: 7

```
atg ctc tct cga cat atc aat tat ttt ctt gcc gtg gct gaa cat ggc    48
Met Leu Ser Arg His Ile Asn Tyr Phe Leu Ala Val Ala Glu His Gly
1               5                   10                  15 agc ttc acc cgt gcc gcc agt gcg ttg cac gtc tcc caa cct gcg ctt    96
Ser Phe Thr Arg Ala Ala Ser Ala Leu His Val Ser Gln Pro Ala Leu
                20                  25                  30 tcc cag cag att cgc cag tta gag gag agt tta ggc gtg ccg ctg ttt   144
Ser Gln Gln Ile Arg Gln Leu Glu Glu Ser Leu Gly Val Pro Leu Phe
            35                  40                  45 gac cgt agc ggg cga acg att cgt ctc act gat gca gga gaa gtc tgg   192
Asp Arg Ser Gly Arg Thr Ile Arg Leu Thr Asp Ala Gly Glu Val Trp
        50                  55                  60 cga cag tac gcc agc cgg gcg tta cag gaa ctg ggg gcg ggt aaa cgg   240
Arg Gln Tyr Ala Ser Arg Ala Leu Gln Glu Leu Gly Ala Gly Lys Arg
65                  70                  75                  80 gcg att cat gat gtt gcc gat ctg acg cga gga tcg ctg cgt atc gcc   288
Ala Ile His Asp Val Ala Asp Leu Thr Arg Gly Ser Leu Arg Ile Ala
                85                  90                  95 gtc acc ccc acc ttt acg agc tac ttt atc ggc ccc tta atg gcg gat   336
Val Thr Pro Thr Phe Thr Ser Tyr Phe Ile Gly Pro Leu Met Ala Asp
            100                 105                 110 ttc tat gcg cgc tat ccc agc atc acg ctc cag cta cag gaa atg tcg   384
Phe Tyr Ala Arg Tyr Pro Ser Ile Thr Leu Gln Leu Gln Glu Met Ser
        115                 120                 125
```

```
cag gag aaa atc gag gat atg ctt tgc cgc gac gag ttg gac gtt ggg      432
Gln Glu Lys Ile Glu Asp Met Leu Cys Arg Asp Glu Leu Asp Val Gly
        130                 135                 140 att gcc ttc gcg cct gtg cat tcg ccg gag ctg gag gca att cct tta      480
Ile Ala Phe Ala Pro Val His Ser Pro Glu Leu Glu Ala Ile Pro Leu
145                 150                 155                 160 ctg aca gaa agt tta gcg tta gtc gtg gcg caa cat cat ccg ctg gcc      528
Leu Thr Glu Ser Leu Ala Leu Val Val Ala Gln His His Pro Leu Ala
                165                 170                 175 gtc cat gaa cag gtg gcg ttg agt cgc ttg cat gat gaa aaa ctg gtc      576
Val His Glu Gln Val Ala Leu Ser Arg Leu His Asp Glu Lys Leu Val
            180                 185                 190 ctg ctc agc gcg gaa ttt gcc acc aga gag caa att gac cac tac tgc      624
Leu Leu Ser Ala Glu Phe Ala Thr Arg Glu Gln Ile Asp His Tyr Cys
                195                 200                 205 gag aaa gcg ggg cta cat cca cag gtg gtc att gag gcg aac tca att      672
Glu Lys Ala Gly Leu His Pro Gln Val Val Ile Glu Ala Asn Ser Ile
210                 215                 220 agc gcg gtt ctg gag ctg att cgc cgc act tcc ctt tcc aca ttg tta      720
Ser Ala Val Leu Glu Leu Ile Arg Arg Thr Ser Leu Ser Thr Leu Leu
225                 230                 235                 240 cca gca gcg att gcc aca caa cat gac ggg ctt aaa gct att tct ctt      768
Pro Ala Ala Ile Ala Thr Gln His Asp Gly Leu Lys Ala Ile Ser Leu
                245                 250                 255 gcc ccg cca cta ctg gag aga acg gcg gtt ttg ttg cgg cgg aaa aat      816
Ala Pro Pro Leu Leu Glu Arg Thr Ala Val Leu Leu Arg Arg Lys Asn
            260                 265                 270 agc tgg cag aca gcc gcc gcg aag gca ttt ttg cac atg gcg ttg gat      864
Ser Trp Gln Thr Ala Ala Ala Lys Ala Phe Leu His Met Ala Leu Asp
        275                 280                 285 aaa tgc gcg gtt gtt ggc gga aat gaa tca cgg tag                      900
Lys Cys Ala Val Val Gly Gly Asn Glu Ser Arg
    290                 295

<210> SEQ ID NO 8
<211> LENGTH: 299
<212> TYPE: PRT
<213> ORGANISM: Escherichia coli

<400> SEQUENCE: 8

Met Leu Ser Arg His Ile Asn Tyr Phe Leu Ala Val Ala Glu His Gly
1               5                   10                  15

Ser Phe Thr Arg Ala Ala Ser Ala Leu His Val Ser Gln Pro Ala Leu
            20                  25                  30

Ser Gln Gln Ile Arg Gln Leu Glu Glu Ser Leu Gly Val Pro Leu Phe
        35                  40                  45

Asp Arg Ser Gly Arg Thr Ile Arg Leu Thr Asp Ala Gly Glu Val Trp
    50                  55                  60

Arg Gln Tyr Ala Ser Arg Ala Leu Gln Glu Leu Gly Ala Gly Lys Arg
65                  70                  75                  80

Ala Ile His Asp Val Ala Asp Leu Thr Arg Gly Ser Leu Arg Ile Ala
                85                  90                  95

Val Thr Pro Thr Phe Thr Ser Tyr Phe Ile Gly Pro Leu Met Ala Asp
            100                 105                 110

Phe Tyr Ala Arg Tyr Pro Ser Ile Thr Leu Gln Leu Gln Glu Met Ser
        115                 120                 125

Gln Glu Lys Ile Glu Asp Met Leu Cys Arg Asp Glu Leu Asp Val Gly
    130                 135                 140

Ile Ala Phe Ala Pro Val His Ser Pro Glu Leu Glu Ala Ile Pro Leu
```

```
                145                 150                 155                 160
Leu Thr Glu Ser Leu Ala Leu Val Val Ala Gln His His Pro Leu Ala
                    165                 170                 175
Val His Glu Gln Val Ala Leu Ser Arg Leu His Asp Glu Lys Leu Val
                180                 185                 190
Leu Leu Ser Ala Glu Phe Ala Thr Arg Glu Gln Ile Asp His Tyr Cys
            195                 200                 205
Glu Lys Ala Gly Leu His Pro Gln Val Val Ile Glu Ala Asn Ser Ile
        210                 215                 220
Ser Ala Val Leu Glu Leu Ile Arg Arg Thr Ser Leu Ser Thr Leu Leu
225                 230                 235                 240
Pro Ala Ala Ile Ala Thr Gln His Asp Gly Leu Lys Ala Ile Ser Leu
                245                 250                 255
Ala Pro Pro Leu Leu Glu Arg Thr Ala Val Leu Leu Arg Arg Lys Asn
                260                 265                 270
Ser Trp Gln Thr Ala Ala Ala Lys Ala Phe Leu His Met Ala Leu Asp
            275                 280                 285
Lys Cys Ala Val Val Gly Gly Asn Glu Ser Arg
        290                 295
```

<210> SEQ ID NO 9
<211> LENGTH: 57
<212> TYPE: DNA
<213> ORGANISM: Artificial
<220> FEATURE:
<223> OTHER INFORMATION: primer P1

<400> SEQUENCE: 9
tctgcctctc attccagaga cagacagagg ttaacgtagt aagccagtat acactcc       57

<210> SEQ ID NO 10
<211> LENGTH: 57
<212> TYPE: DNA
<213> ORGANISM: Artificial
<220> FEATURE:
<223> OTHER INFORMATION: primer P2

<400> SEQUENCE: 10
aatcatggtg gaactcctga tggtttaaaa ataaggttaa gggcaccaat aactgcc       57

<210> SEQ ID NO 11
<211> LENGTH: 21
<212> TYPE: DNA
<213> ORGANISM: Artificial
<220> FEATURE:
<223> OTHER INFORMATION: primer P3

<400> SEQUENCE: 11
tttaccttat gacaatcggc g                                              21

<210> SEQ ID NO 12
<211> LENGTH: 22
<212> TYPE: DNA
<213> ORGANISM: Artificial
<220> FEATURE:
<223> OTHER INFORMATION: primer P4

<400> SEQUENCE: 12
aagatcaaga cgaatattgc gg                                             22